Figure 1:
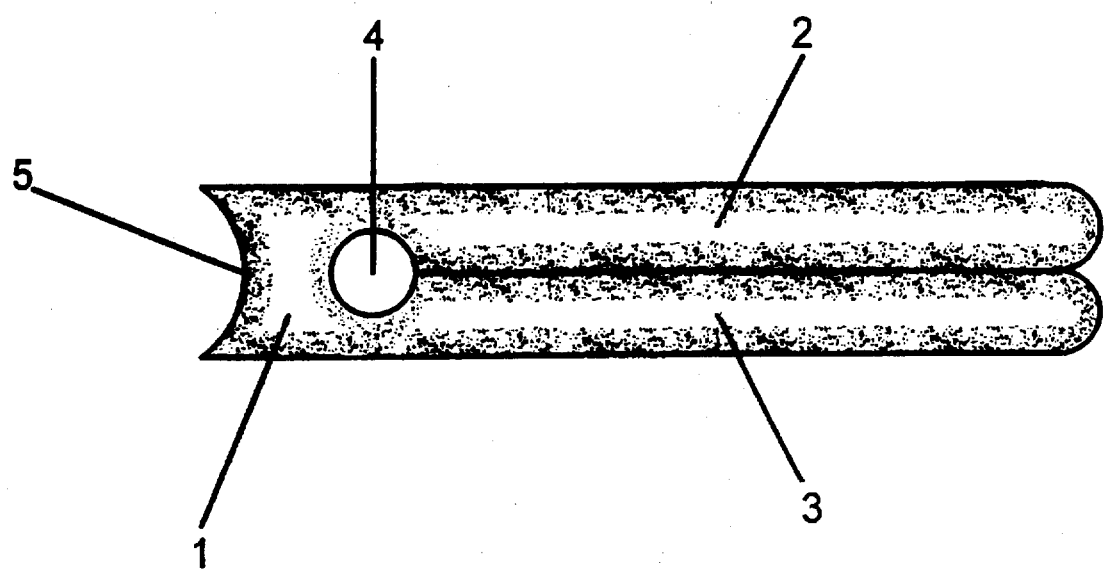

United States Patent [19]

Staudinger

[11] Patent Number: 5,711,312
[45] Date of Patent: Jan. 27, 1998

[54] SELF-ADHESIVE READY-TO-USE SUPPORT FOR THE PATELLA

[75] Inventor: Peter Staudinger, Tornesch, Germany

[73] Assignee: Beiersdorf AG, Hamburg, Germany

[21] Appl. No.: 676,015

[22] Filed: Jul. 5, 1996

[51] Int. Cl.[6] .................................................. A61F 15/00
[52] U.S. Cl. ............................. 128/845; 602/23; 602/26
[58] Field of Search ........................................ 128/845, 846, 128/882, 892, 893; 602/5, 23, 26, 57, 60, 61

[56] References Cited

U.S. PATENT DOCUMENTS

| | | |
|---|---|---|
| 4,423,720 | 1/1984 | Meier et al. . |
| 5,139,476 | 8/1992 | Peters .................................. 602/26 |
| 5,139,477 | 8/1992 | Peters .................................. 602/26 |
| 5,277,697 | 1/1994 | Frances ............................... 602/26 |
| 5,503,908 | 4/1996 | Faass . |

FOREIGN PATENT DOCUMENTS

| | | |
|---|---|---|
| 32 42 592 A1 | 5/1984 | Germany . |
| 3242592 | 5/1984 | Germany . |
| 9219189 | 4/1992 | WIPO . |
| WO92/19189 | 11/1992 | WIPO . |

*Primary Examiner*—Michael A. Brown
*Attorney, Agent, or Firm*—Sprung Kramer Schaefer & Briscoe

[57] ABSTRACT

Ready-to-use support with a self-adhesive coating on one side for stabilizing and guiding the patella, characterized in that the ready-to-use support consists of an elongate strip which has, approximately over the entire length, a slit in the longitudinal direction on one side, and in that a cutout is located at the inner end of the slit and serves to receive the patella when the ready-to-use support is applied to the knee.

9 Claims, 2 Drawing Sheets

SELF-ADHESIVE READY-TO-USE SUPPORT FOR THE PATELLA

DESCRIPTION

The invention relates to a ready-to-use support, which has a self-adhesive coating on one side, for stabilizing and guiding the patella in its natural slide bearing.

The functional bandaging technique called taping is a treatment method for the prophylaxis and therapy of injuries, disorders and changes in the locomotor system. The aim of taping is specifically to simulate the capsule/ligament structures and thus achieve selective support and stabilization.

The actual taping bandage is for this purpose applied stripwise from preferably inelastic self-adhesive tapes, called straps, or in conjunction with self-adhesive tapes with short-stretch elasticity. It protects, supports and relieves portions of a functional unit which are at risk, damaged or impaired. It permits functional loading in the pain-free movement range but prevents extreme or painful movements.

However, the application of such bandages requires expert skill and experience and therefore, as a rule, cannot be carried out by laypeople without taping experience.

An additional difficulty specifically in the region of the knee joint is that the hollow of the knee is in most cases covered with bandaging material, and thus flexion of the knee is not sufficiently possible. So-called ready-to-use supports of elastic fabric or neoprenes have the disadvantage that they are not adequately fixed to the skin and thus may act only globally on a large area, not selectively. Specific stabilization and guidance is impossible in most cases.

It was therefore an object of the invention to provide a ready-to-use support which, by reason of its design, its material and its properties, is suitable for prophylactic support and selective guidance of the patella and which can be applied in a simple manner even by the user.

This object is achieved by a ready-to-use support according to claim 1.

It has proved particularly advantageous to have a circular cutout which is located in the middle of the strip and which has a diameter of about 4 cm suited to the size of the patella. This makes it possible to employ the ready-to-use support according to the invention universally for guiding the patella to prevent lateralization, that is to say displacement sideways of the patella, or medialization, that is to say displacement of the patella parallel to the vertical axis of the body.

The strips of the ready-to-use support have a length of about 1 m, preferably about 80 cm, with the unslit part of the strip being about 8 cm long and 10 cm wide, and the two strips produced by the slit each being about 68 cm long and 5 cm wide. Thus, with the cutout, which has a length of about 4 cm, the resulting total length of the ready-to-use support is about 80 cm.

The ready-to-use support preferably consists of a longitudinally elastic woven or knitted fabric which may, where appropriate, also have a slight transverse elasticity, in particular based on cotton. The longitudinal elasticity preferably corresponds to that of so-called short-stretch bandages, that is to say bandages with an extensibility of about 60–90%.

In order to relieve the leg muscles, the ready-to-use support should be applied with the knee slightly flexed. For this reason, the unslit narrow side of the strip preferably has a concave curvature which reproduces the curve of the knee and thus facilitates application of the ready-to-use support to the knee joint.

It is advantageous, in order to make it easy to pull the ready-to-use support off the knee joint, for the ends of the two strips which are separated by the slit to have a convex curvature.

The ready-to-use support is coated on the side which is placed on the skin with one of the known self-adhesive compositions which are based on rubber or synthetic polymers and which adhere well. The compositions advantageously have other properties such as good compatibility with skin or permeability to air and water vapour.

Until the support is used, the adhesive layer is covered with a sheet material with an abherent finish, such as, for example, siliconized paper or plastic film.

In this connection, it has proved to be particularly user-friendly to divide the covering into several individual parts, preferably three parts. One part covers the unslit part, and in each case one other strip-shaped part covers the narrow strips of the ready-to-use support. In order further to facilitate application, these individual covering parts can also be appropriately visually distinguished.

FIG. 1 shows the ready-to-use support in its preferred embodiment. The ready-to-use support is composed of the unslit part (1) and of the strips (2) and (3) produced by the slit, called the straps. The unslit part (1) has a concave curvature (5), and the two strips (2) and (3) have a convex one.

Figure 2:
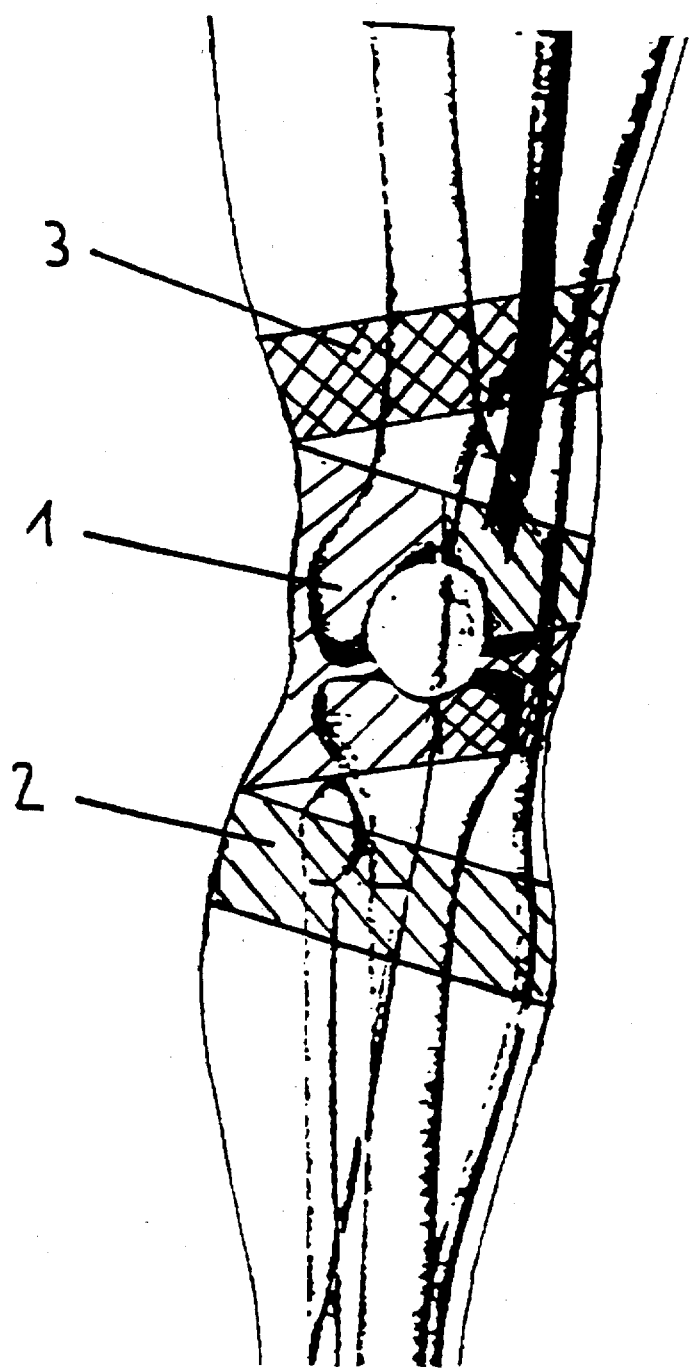

FIG. 2 depicts the preferred embodiment of the ready-to-use support as applied to the knee joint to immobilize the patella against lateralization. In the first step, the covering paper is pulled off the unslit part (1) of the ready-to-use support. The unslit part (1) of the ready-to-use support is subsequently applied laterally to the knee joint which is flexed in a small angle of, preferably, 20°–30° in such a way that the circular cutout (4) in the ready-to-use support firmly encloses the patella, and the two straps (2) and (3) point in the medial direction. After removal of the covering paper on the strap (2) which is in proximal/ventral contact with the patella, the strap is guided distally with a slightly spiral movement around the leg. The strap (2) is moreover guided dorsally in such a way that the hollow of the knee remains substantially uncovered. The end of the strap (2) on the lower leg is located on the ventral side. The strap (3) which is in distal/ventral contact with the patella is applied analogously after the covering paper has previously been pulled off. The strap (3) is applied proximally, with a spiral movement, to the leg. The two straps (2) and (3) cross over on the medial part of the patella in order thus to provide the patella with the required support. The second strap (3) is also placed in such a way that, on the one hand, the dorsal portion of the hollow of the knee is left substantially uncovered and, on the other hand, the end thereof is located on the ventral side on the thigh.

The described mode of application of the ready-to-use support results in stabilization of the patella and, at the same time, lateralization of the latter is counteracted. The strap (2) provides distal and lateral support for the patella, and strap (3) provides proximal and lateral support. Hence unwanted lateral movement of the patella is substantially precluded.

Alternatively, the ready-to-use strap can, however, also restrict medialization of the patella, in that the unslit part (1) of the ready-to-use support is firmly applied distally or proximally to the patella, and the straps (2) and (3) are subsequently stuck on in analogy to that described above.

I claim:

1. Ready-to-use support with a self-adhesive coating on one side for stabilizing and guiding the patella, characterized in that the ready-to-use support consists of an elongate strip which has, approximately over the entire length, a slit in the longitudinal direction on one side, and in that a cutout is located at the inner end of the slit and serves to receive the patella when the ready-to-use support is applied to the knee.

2. Self-adhesive ready-to-use support according to claim 1, characterized in that the cutout has the shape of a circle with a diameter of approximately 4 cm which, relative to the width of the strip, is located in the middle of the latter.

3. Self-adhesive ready-to-use support according to claim 1, characterized in that the unslit part (1) of the strip is about 8 cm long and 10 cm wide, and the two strips (2) and (3) produced by the slit are each about 68 cm long and 5 cm wide.

4. Self-adhesive ready-to-use support according to claims 1, characterized in that the ready-to-use support can be employed universally for guiding the patella to prevent lateralization, that is to say displacement sideways of the patella, or medialization, that is to say displacement of the patella parallel to the vertical axis of the body.

5. Self-adhesive ready-to-use support according to claim 1, characterized in that the ready-to-use support consists of a longitudinally elastic woven or knitted fabric.

6. Self-adhesive ready-to-use support according to claim 1, characterized in that the unslit part (1) of the strip has a concave curvature.

7. Self-adhesive ready-to-use support according to claim 1, characterized in that the ends of the two strips (2) and (3) separated by the slit have a convex curvature.

8. Self-adhesive ready-to-use support according to claim 1, characterized in that the ready-to-use support is covered on its self-adhesive side with abherent material.

9. Self-adhesive ready-to-use support according to claim 8, characterized in that the abherent material is designed in three parts, one part covering the unslit part and one other part in each case covering the narrow strips.

* * * * *